United States Patent [19]

Poley

[11] Patent Number: 4,988,352

[45] Date of Patent: Jan. 29, 1991

[54] METHOD AND APPARATUS FOR FOLDING, FREEZING AND IMPLANTING INTRAOCULAR LENS

[76] Inventor: Brooks J. Poley, 2 Greenway Gables, Minneapolis, Minn. 55403

[21] Appl. No.: 416,361

[22] Filed: Oct. 3, 1989

Related U.S. Application Data

[63] Continuation-in-part of Ser. No. 345,837, May 1, 1989, Pat. No. 4,917,690, and Ser. No. 213,325, Jun. 30, 1988, Pat. No. 4,911,714, which is a continuation-in-part of Ser. No. 31,250, Mar. 26, 1987, Pat. No. 4,769,034.

[51] Int. Cl.⁵ .......................... A61B 17/00; A61F 2/16
[52] U.S. Cl. ......................................... 606/107; 623/6
[58] Field of Search .......................... 606/107; 623/6

[56] References Cited

U.S. PATENT DOCUMENTS

| | | | |
|---|---|---|---|
| 4,534,069 | 8/1985 | Kelman | 623/6 |
| 4,573,998 | 3/1986 | Mazzocco | 606/107 X |
| 4,619,662 | 10/1986 | Juergens | 623/6 |
| 4,681,102 | 7/1987 | Bartell | 623/6 |
| 4,731,079 | 3/1988 | Stoy | 606/107 X |
| 4,769,034 | 9/1988 | Poley | 623/6 |
| 4,781,719 | 11/1988 | Kelman | 623/6 |
| 4,819,631 | 4/1989 | Poley | 623/6 |
| 4,946,470 | 8/1990 | Sulc | 623/6 |
| 4,955,889 | 9/1990 | Van Gent | 606/107 |

OTHER PUBLICATIONS

V. L. Bohn, "Soft IOL Technology", Ocular Surgery News, vol. 5, No. 5, Mar. 1, 1987, p. 1.
Brochure—Frigitronics CE-82; "An Advanced Ophthalmic Cryosurgical System", 1988.

*Primary Examiner*—Alan Cannon
*Assistant Examiner*—David H. Willse
*Attorney, Agent, or Firm*—Wood, Herron & Evans

[57] ABSTRACT

An intraocular lens, folded on itself for insertion into an eye, is retained in the folded configuration by chilling until it becomes inflexible and loses its tendency to unfold. The folded, frozen lens is inserted into the eye and thaws in situ to restore it to its original unfolded configuration. The chilling obviates the need for special retaining means to hold the lens in the folded configuration for insertion, thereby facilitating the surgical procedure and enabling a smaller incision to be used. The lens may be frozen onto an inserter for positioning it within the eye. Apparatus for folding and freezing the lens is also disclosed.

33 Claims, 3 Drawing Sheets

METHOD AND APPARATUS FOR FOLDING, FREEZING AND IMPLANTING INTRAOCULAR LENS

RELATED APPLICATIONS

This application is a continuation-in-part of my co-pending applications Ser. No. 345,837, filed May 1, 1989titled "Folded Intraocular Lens With Endless Band Retainer", now U.S. Pat. No. 4,917,690, and Ser. No. 213,325, filed June 30, 1988, titled "Foldable Intraocular Lens and Improved Fold Retaining Means", now U.S. Pat. No. 4,911,714. The latter application is a continuation-in-part of my Ser. No. 31,250, filed Mar. 26, 1987, now U.S. Pat. No. 4,769,034, issued Sept. 6, 1988, titled "Folded Intraocular Lens, Method of Implanting Folded Intraocular Lens." My U.S. Pat. No. 4,819,631, issued Apr. 11, 1989, titled "Folded Intraocular Lens, Method of Implanting It, Retainer, and Apparatus for Folding Lens" is a division of U.S. Pat. No. 4,769,034.

FIELD OF THE INVENTION

This invention relates generally to the implanting of intraocular lenses to replace the natural lens in the eye. More specifically it relates to means for holding an intraocular lens in a folded configuration for implanting.

BACKGROUND

The use of intraocular lenses ("IOLs") has been highly developed in recent years, especially for implanting after the removal of cataracts, and such operations are now common medical procedures. In such procedures it is desirable to minimize the size of the incision which must be made to insert and position the IOL in the eye, in order to shorten the time required for healing and to minimize any chance of failure. Most implanting techniques have required that the incision in the eye be slightly wider than the diameter of the IOL to be implanted so that the lens can be inserted through the incision.

Recently, techniques have been developed for reducing the width of certain lenses by folding them prior to insertion, see V. L. Bohn, "Soft IOL Technology", *Ocular Surgery News*, Vol. 5, No. 5, Mar. 1, 1987, page 1. The use of a folded lens enables a smaller incision to be used than would otherwise be required; for example, a lens of 6.5 mm. diameter can, if folded, be inserted through an incision only 3.5 mm. wide.

My U.S. Pat. No. 4,769,034, previously referred to, discloses a foldable resilient lens which is retained in a folded configuration for implanting, by a retainer which is wrapped around the lens and temporarily held in place around the folded lens by ties. That enables the lens to be inserted through the same small incision which is used to remove a cataract from the eye. My co-pending application Ser. No. 213,325, previously referred to, discloses other means for retaining a folded lens, including a retainer which is integral with the lens itself, or alternatively sutures which extend through apertures in overlying parts of the folded lens. However, those techniques are relatively complicated in that they require securing a retainer around the lens, or suturing through the folded lens, or forming a retainer integrally with the lens.

My copending application Ser. No. 345,837, also previously referred to, discloses a lens which is held in the folded configuration by a retainer in the form of a pliable, severable endless band which extends around the lens. Once the lens has been inserted in the eye, the endless band is removed as by severing it lengthwise. However, placing the endless band around the folded lens will in practice typically be done at the point of production and requires a lens material with a long "memory" so that the lens will reopen to its original unfolded configuration and regain good optical properties even after having been folded for a protracted period. Some IOL materials, when folded, do not have a good "memory" of their original shape; they do not quickly return to their original design configuration. Further, the implanting technique requires the development of some skill on the part of the surgeon to release the band, otherwise the unfolding may be jerky and may cause stabilization problems.

Bartell U.S. Pat. No. 4,681,102 discloses a technique wherein an IOL is folded by rolling it up, and is then placed in a hollow injector or "shooter." A plunger pushes the IOL through an open end of the injector into the eye. It is difficult to insert the IOL into the injector at the point of surgery, and the lens design must accommodate the requirements of the injector. Moreover, the technique affords relatively poor control of the IOL during release; movement of the leaves of the lens is uncontrolled as they open from the rolled configuration. This raises a possibility that a part or leaf of the lens may strike the backside of the cornea and really damage the eye.

The Faulkner forceps, sold by Katena Corporation, are specially designed to compress and surround a lens for insertion into the eye. As in the shooter technique, a larger incision is required to accommodate the forceps-held lens. Generally that technique requires that the incision be somewhat wider, for example 4.5 mm rather than 3.5 mm. Further, after the lens has been inserted in the eye it is rather awkward to open the forceps jaws, and the surgeon has relatively poor control of the unfolding movement of the lens during this phase. Either the lens or the jaws of the forceps can strike and injure the cornea.

Thus there is a need for a technique to hold a lens in a folded configuration which (a) does not require a larger surgical incision than is used for cataract removal; (b) can quickly and easily be used at the time and place of use to fold and retain the lens; and (c) can easily be controlled to prevent possible injury to the cornea in implanting.

SUMMARY OF INVENTION

In accordance with this invention, I have found that a folded intraocular lens can be retained in the folded configuration for implanting, by "freezing" the folded lens sufficiently that it loses flexibility and becomes rigidified in the folded configuration. The plastic materials which are commonly used to make IOLs, including acrylics as well as silicones, lose flexibility with decreasing temperature. At temperatures substantially below body temperature, for example, in the approximate range of −20° to −60° F., a folded IOL does not unfold, but when returned to normal temperature, it unfolds and returns to original shape without apparent loss of quality.

The term "freezing" is used herein to refer to the step of rigidifying a folded, normally flexible lens by chilling the lens so that it does not spontaneously unfold while it remains chilled. In this context "freezing" does not necessarily require conversion of a liquid to a solid, although water droplets dispersed within the lens material may in fact freeze to ice. (It should be noted, however, that water or another normally liquid material which converts from a liquid to a solid state at a temperature substantially below body temperature, may be used to assist in freezing in lens.)

Similarly, "thawing" is meant to denote the reverse step, i.e., the return of the lens from a rigid frozen state to a pliable state such that the lens unfolds. Thawing occurs surprisingly quickly within the eye and restores the lens to its unfolded configuration. Because the thawing unfolds the lens, there is no separate retainer to cut, unlatch or remove. No bulky injector or forceps is needed. Nothing adds to the width of the folded lens, so that a minimum incision size is sufficient.

In accordance with another aspect of the invention, I have invented a special insertion tool for freezing, carrying, and positioning the folded lens. The inserter has a blade with a "teardrop" or airfoil cross-sectional shape that corresponds to the space between the opposed leaves of the lens. The lens is preferably folded in half, like a taco, around the blade. The teardrop shape of the inserter blade prevents the lens from being creased along a fold axis, yet holds the lens so that it can be manipulated in insertion. Unlike a retainer around the outside of a lens, this "internal" retainer does not necessarily add to the cross sectional area or width of the folded lens.

In a preferred embodiment a combination inserter/freezer is provided which freezes the lens by cryogenically chilling the inserter blade about which the lens is folded. The inserter/freezer has internal heat transfer means for chilling the blade, so that the lens is frozen from the blade outwardly; that is, the heat content of the lens is transferred inwardly to the blade. This provides a surprising advantage, in that the outside face of the folded lens can be at a somewhat higher temperature than its inside face, which is adjacent the cold blade; the inside part of the lens can be chilled sufficiently to prevent the lens from unfolding, while the outside remains relatively warmer so as not to freeze or stick to eye tissue.

I have further found that the common lens materials, when frozen, tend to adhere to a metal inserter blade, somewhat as an ice cube adheres to a metal cube tray. This characteristic can be used to adhere the lens to the inserter blade: the lens can be frozen on the blade like an ice-cream bar is frozen on a stick. The inserter thereafter carries the lens more securely and enables it to be inserted and positioned more easily.

Lens folding apparatus is also provided. The folding apparatus may be generally like the lens compressor which is disclosed and claimed in my U.S. Pat. No. 4,819,631, previously referred to, but is provided with special means for receiving and positioning the inserter in precise relation to the lens prior to folding. The folding apparatus may have means for applying a cryogenic cooling medium to freeze the lens or to assist an inserter/freezer in freezing the lens.

DESCRIPTION OF THE DRAWINGS

The invention can best be further described by reference to the accompanying drawings, in which.

FIG. 2 is a top plan view of the apparatus, showing an inserter in the apparatus with its blade positioned on a lens, prior to folding;

FIG. 3 is a vertical section taken on line 3—3 of FIG. 2, but shows the lens being folded;

FIG. 4 is similar to FIG. 3 but shows the apparatus in closed position with the lens folded around the inserter blade, ready for freezing;

FIG. 6 is a diagrammatic view of an eye being prepared for implanting the folded, frozen lens;

FIG. 7 is a view similar to FIG. 6 but shows the lens being inserted with the inserter;

FIG. 8 shows the lens, still on the inserter, positioned in the eye, with a second instrument inserted through a separate, smaller incision to control lens unfolding;

FIG. 9 shows the thawed lens, unfolded within the eye, prior to removal of the inserter; and FIG. 10 shows the unfolded lens centered in the eye after removal of the inserter.

DETAILED DESCRIPTION OF INVENTION

The invention may be used in conjunction with resiliently foldable intraocular lenses of known type, for example the acrylic lens made by Ioptics, Inc. or the silicone lens made by American Medical Optics, Inc. A unique lens material is not required; many, if indeed not all, commonly used foldable IOL materials appear to be freezable in accordance with the invention. The only limitation on the material is that it become sufficiently rigid at a temperature substantially below normal body temperature (e.g., below roughly about $-20°$ C.) that the lens does not unfold until it is warmed. Lenses of the conventional acrylic or silicone materials are presently preferred.

The lens can be frozen by any chilling means which produces a suitably low temperature; no special refrigerant or apparatus is required. It is preferred that the lens be frozen while it is folded around an inserter by apparatus as described hereinafter, but it should be understood that the lens can be folded and held by other means, including various types of retainers, until frozen. It is highly desirable, however, that any retainer used to hold the lens folded until frozen be removed prior to implanting the lens.

Figure 1:
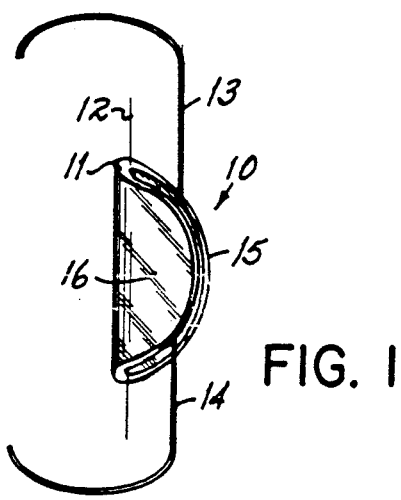
FIG. 1 is an enlarged perspective view of an IOL which has been folded and frozen in accordance with the invention.

In FIG. 1, a lens which has been folded and frozen in accordance with the invention is designated generally by 10. (The term "folded," as used herein, is meant to include rolling as well as folding about more than one axis of folding.) The lens may have a circular or elliptical periphery or margin 11, and is preferably folded once, that is, in half. It is not creased or folded flat along its diameter or an axis of folding 12, which could critically alter its optical properties after unfolding. A pair of haptics 13 and 14 extend from opposite positions on periphery 11. The upper haptic 13 is referred to as the "6 o'clock" haptic and the lower haptic 14 is referred to as the "12 o'clock" haptic. When inserted in an eye this folded configuration, the rear leaf or half 15 of a singly folded lens is the posterior leaf, while the front leaf 16 is the anterior leaf.

Figure 4:
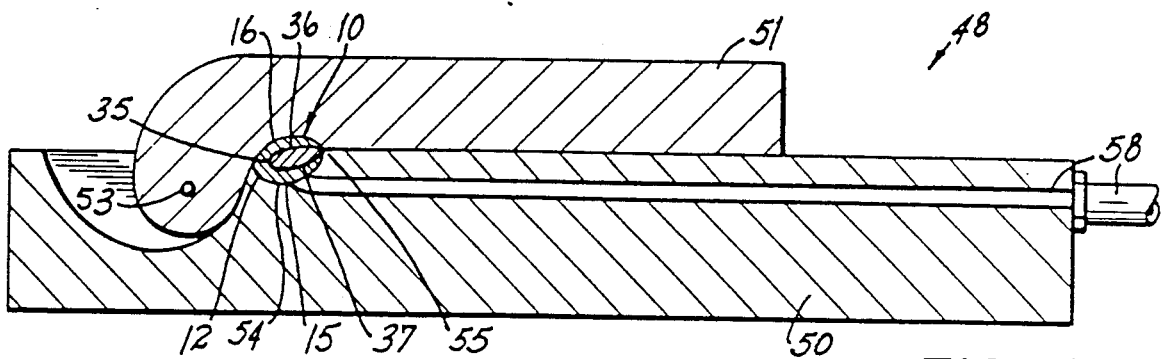
Figure 5:
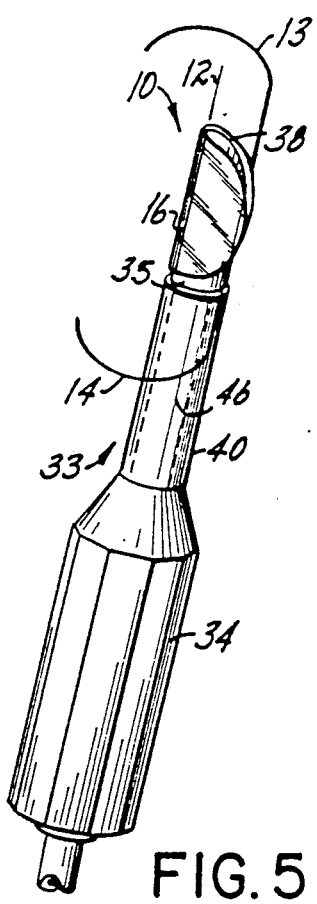
FIG. 5 shows a preferred form of inserter with a lens folded and frozen on its blade.

The folded, frozen lens is preferably carried on an inserter 33 as best shown in FIG. 5. The inserter can serve to hold the lens for folding and freezing; to carry the folded, frozen lens to the incision; to insert the lens through the incision; and/or to position and manipulate the lens within the eye. (And, as will be described later in more detail, the inserter can also freeze the lens.) The inserter has a handle 34 which at one end removably mounts a blade 35 having an upper face 36 and lower face 37 (see FIGS. 3 and 4). In cross section blade 35 is preferably shaped like a teardrop or airfoil corresponding to the shape of the gap or space 38 between the posterior and anterior leaves of the folded lens. The opposite blade faces should at least partially engage the respective leaves of the lens. Blade 35 is preferably of metal, and has a shank 40 which extends into and is seated in handle 34 of the inserter.

The inserter preferably includes internal cooling means by which it can function as a combination freezer/inserter. To this end, a coolant line 41, which may be a flexible insulated conduit, extends into the handle of the inserter in heat transfer relationship with the blade shank 40. Coolant line 41 is connected to an external coolant source 42 and may include a return line. The coolant source 42 may include a control valve 43 for regulating the rate of flow of fluid in line 41, and hence the temperature of the blade and indirectly, of the lens. In order to minimize contact between cold metal and eye surfaces the exposed portion of the blade shank may be insulated with a protective, non-stick plastic sleeve 46.

From the foregoing it can be seen that the freezer/inserter freezes the lens by cooling it through the blade. By controlling the rate of coolant flow to the blade the lens can be frozen, or maintained frozen in air or in liquid, and its thawing can be regulated to provide unfolding at the desired time. Frigitronics Corporation produces and sells a "Frigitronic Ophthalmic Cryo Surgical Device", Model CE-82. That device has heretofore been used to remove cataracts, freeze retinal areas, and to destroy ocular tissue such as the iris and cornea by freezing it in the eye. As sold, that device has a round, rod-like freezing tip having a shank which is removably seated in a handle. The shank is cooled in the handle by a gas, typically nitrous oxide ($N_2O$) gas, from an external source of cryogenic fluid. By controlling the rate of gas flow the temperature of the tip can be set at a desired temperature from 0° C. to about −90° C., and for that purpose the gas flow controller is calibrated in degrees. While that device as sold is not suitable to fold or freeze an IOL on a blade in accordance with this invention, it is illustrative of one type of hand holdable, controllable freezing means which can be modified with a blade as described herein (instead of its usual round rod tip). So modified the lens can be frozen by heat transfer to the chilled blade, and then handled and inserted in accordance with this invention.

As previously indicated, freezing the lens from the "inside out" (by contact of the inside lens face with the chilled blade), rather than "outside in" (by contact of the outside face of the folded lens with a coolant medium) provides an important advantage. By freezing in this manner, the inside part of the lens adjacent the cold blade, is colder, whereas the outside, somewhat insulated from the inside by the thickness of the lens, is relatively warmer. The resulting temperature differential across the folded lens enables the inside to be chilled until frozen so as to hold the lens rigid, while the outside remains sufficiently warmer so as not to stick or adhere to the incision or internal eye tissue.

The nature of the coolant is not critical. A cryogenic fluid such as gas evaporated from liquid $N_2O$, $N_2$, or $O_2$, or $CO_2$ from dry ice can be used, by way of example. If a lens of acrylic is immersed in liquid nitrogen, the lens will freeze to rigidity within a few seconds; cryogenic $NO_2$ gas requires somewhat longer. The lens should be frozen at as high a temperature as will rigidify it sufficiently for implanting, so as to minimize any chance of damage to eye tissue by freezing.

Different lens materials freeze to rigidity at somewhat different temperatures; acrylics freeze at higher temperatures than silicones. The optimum temperature to be maintained varies with lens thickness and dioptric power, the higher powered, thicker lenses require cooler temperatures to remain frozen in air. To adjust for these factors it is contemplated that the control valve 43 can be calibrated to correspond to different degrees of cooling for different lens materials and sizes. Valve 43 can have various pre-established settings to control flow at different specific rates for a given lens material and size; at a low rate when the lens, frozen on the blade, is in air (prior to insertion); at a higher rate after the lens, on the blade, has been inserted in the liquid within the eye, prior to unfolding; and closed, to permit rapid thawing to take place in the eye. A multiple setting foot controlled valve is useful to enable the physician to make such changes in flow rate during the implanting operation. Optionally, the inserter may include a selectively operable resistive heater to promote more rapid thawing. A temperature sensing device may be provided on the inserter to provide an indication of lens or blade temperature so the physician is enabled to know how close the lens is to unfolding.

Freezing the lens in contact with the blade tends to cause the lens to adhere to the blade. This provides a convenient grip on the lens and facilitates carrying it to the incision, inserting, and positioning in the eye before unfolding. It is contemplated that either the lens, the blade or both may be misted with an adhesion promoting liquid material, e.g., water or saline solution to assist in adhering the lens to the blade. However, while adherence of the folded lens to the inserter is desirable it is not necessary, and a blade of non-adherent material such as Teflon may be used.

The frozen lens will remain in the folded configuration only for a short period of time if no further cooling is applied, and then will thaw and unfold to its original shape. For a lens frozen by immersion in liquid nitrogen, thawing requires about a minute in air. Warming is of course much more rapid in the liquid of the eye; in liquid at a temperature of 95°–100° F. a folded lens unfolds in as little as five seconds. If the lens is carried on an inserter which is internally cooled, the time of lens unfolding can be delayed and controlled by the physician.

Although the lens can be folded and frozen separately and then placed on the blade of an inserter, for the reasons just given it is highly desirable just to fold the lens around an inserter blade and then freeze it on the blade.

Figure 2:
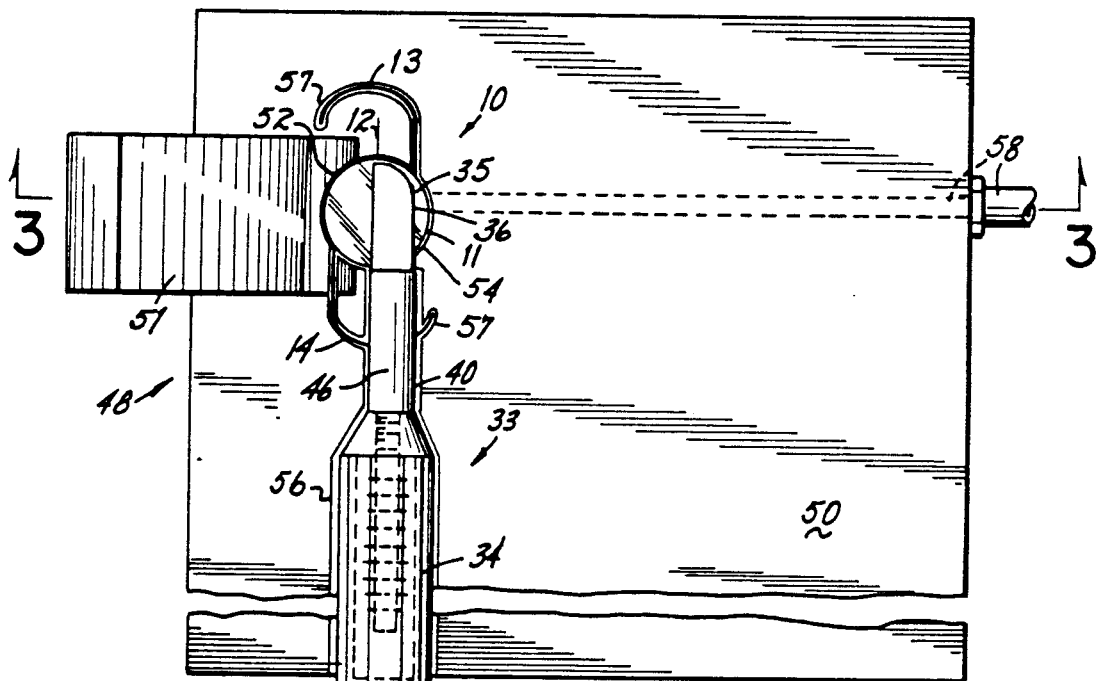
FIGS. 2-4 illustrate a preferred form of folding and freezing apparatus for use in practicing the invention. More specifically.
Figure 3:
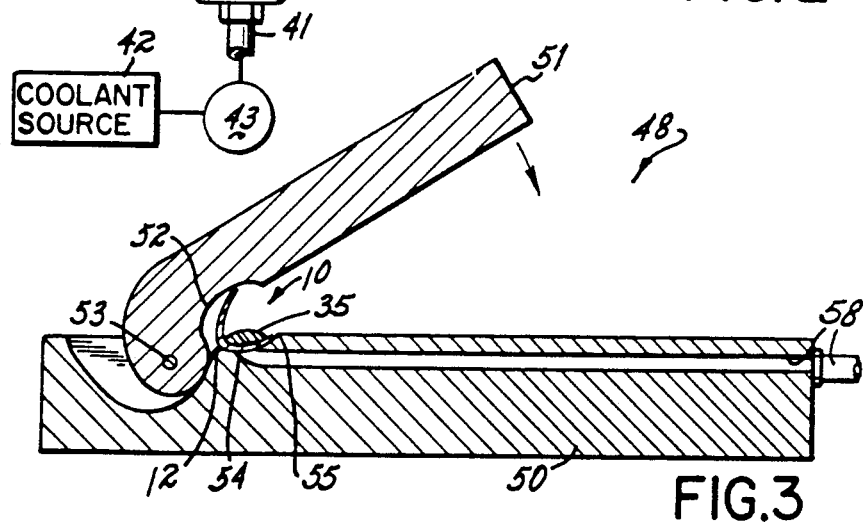

To facilitate folding the lens around an inserter blade, I have provided apparatus as shown in FIGS. 2–4. A related type of lens folding apparatus is described in my previously identified U.S. Pat. No. 4,819,631, to which reference may be had for a further description. However, that patent does not contemplate folding a lens on an inserter. The preferred folding and freezing apparatus 48 includes a base 50 and a folding arm 51 which is hinged to the base. A lens folding cavity 52 is defined by and between handle 51 and base 50, adjacent handle hinge axis 53. The base cavity portion 54 has a seat on which one face of the lens rests horizontally. An overhanging abutment or lip 55 helps to retain the lens in the cavity for folding. A recess or socket 56 is provided in the base 50 to receive the handle 34 of the inserter so that blade 35 thereof is positioned properly on the other (upper) face of the lens in cavity 52. Socket 56 is parallel to hinge axis 53. The base lens cavity 54 includes curved recesses 57 to receive the haptics 13 and 14. The handle and base surfaces which contact the lens should preferably be non-adherent. When arm 51 is folded over (to the right in FIG. 4), the anterior half of the lens is folded from the left side of blade 35 over the top of the blade so that the blade 35 is then sandwiched between the respective halves of the lens. The lens is then ready to be frozen.

To assist in freezing the lens, or if the inserter has inadequate cooling capacity, the folding apparatus may be provided with a coolant passage 58 which opens to cavity 52. Passage 58 is connected to a source of a cryogenic (freezing) gas or liquid. This fluid flows into the cavity via passage 58 to freeze or help freeze the lens after it has been folded over the blade.

After the lens has been frozen arm 51 is swung open and the inserter, with lens frozen on it, is removed. As already described, coolant is desirably supplied to the inserter handle 34, to slow the otherwise rapid rate of warming in air.

Figure 6:
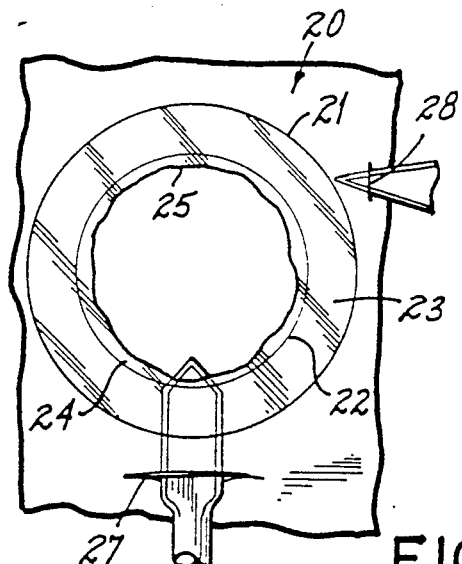
FIGS. 6-10 are a series of views which illustrate the implanting of a lens in accordance with a preferred embodiment of the invention. More specifically.
Figure 7:
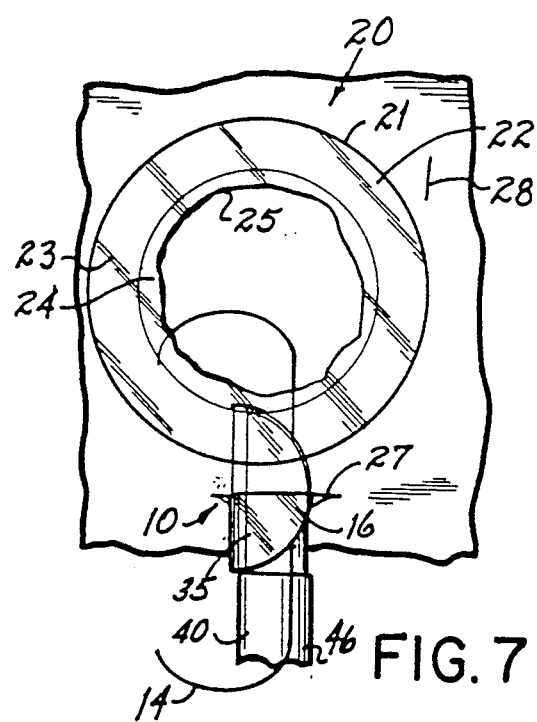
Figure 8:
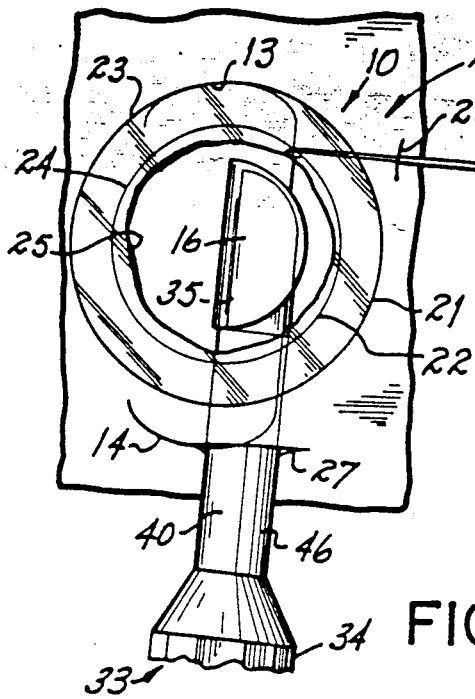
Figure 9:
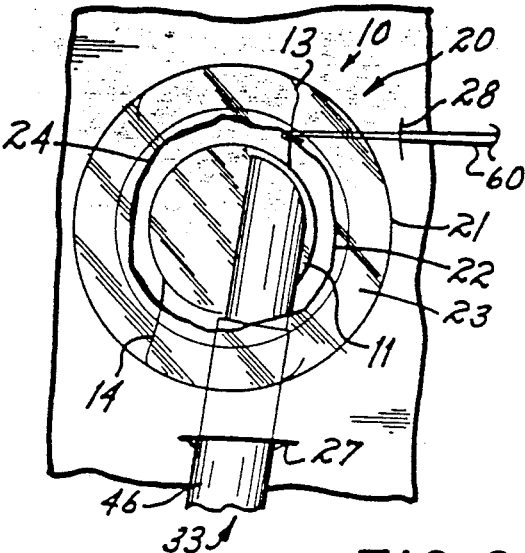

FIG. 6 illustrates diagrammatically an eye 20 being prepared for a lens implant. The limbus or outer margin of the cornea is designated by 21 and the pupil margin by 22. The area between the limbus and the pupil margin is the iris (the blue or brown portion) 23 of the eye. The capsule 24 containing the natural lens is cut away to receive the IOL, as designated by 25, in accordance with conventional practice. The cataracted natural lens may be removed by any conventional technique, but preferably is removed by phakoemulsification, because it requires an incision which may be as small as 3.2 mm wide, just large enough to admit the folded lens. The technique for implanting the folded frozen lens requires a primary incision 27 of width dictated by the width of the folded lens. I have found that the folded, frozen lens is sufficiently rigid that it can easily be inserted through a conventional phakoemulsification incision. Preferably a secondary incision 28 is made at the 9 o'clock position.

Figure 10:
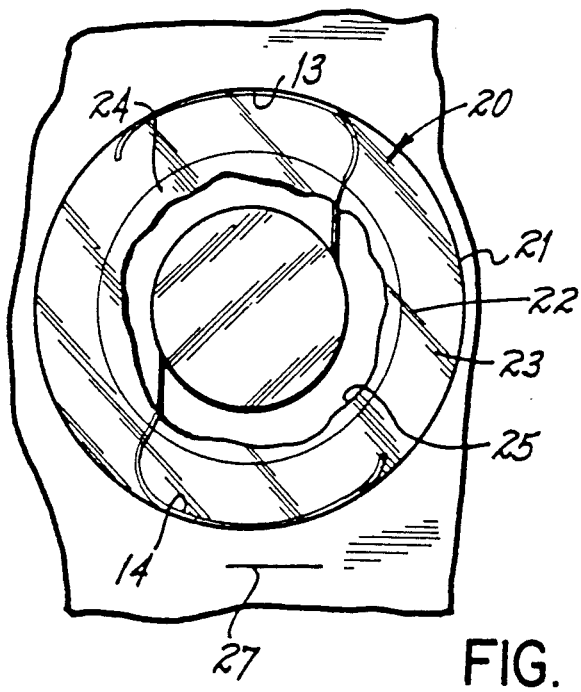

Implanting the lens in an eye is shown in FIGS. 6–10. The folded, frozen lens, preferably carried on the blade of an inserter, is slipped through the primary incision 27, the 6 o'clock haptic 13 being inserted first. The technique for inserting the lens may generally follow that described in my U.S. Pat. No. 4,769,034, previously identified, to which reference should be had, with the difference that unlike that patent, here there is no separate retainer to be removed. Once the lens has been positioned within the eye coolant to the blade is interrupted and the lens warms rapidly and thereby releases itself from the inserter. During thawing and unfolding of the lens, it is desirable to stabilize the movement of the anterior leaf with the use of a secondary instrument for better control. An instrument having a hook 60 is inserted through secondary incision 28 and engages the 6 o'clock haptic 13. The 12 o'clock haptic of the upper lens half projects outside the primary incision during this stage and rotates 180°, moving from the position shown in FIG. 8 to that in FIG. 9. Haptic 14 is then seated within the lens capsule, the lens is centered, and the instruments removed (FIG. 10). The incisions are closed in the conventional manner.

Having described the invention, what is claimed is:

1. The method comprising,
   folding an intraocular lens about a blade,
   applying cooling to said blade to cool the lens folded about said blade, and
   reducing the temperature of the blade sufficiently that the lens is rigidified in the folded configuration on the blade.

2. The method of claim 1 wherein said blade is cooled to a temperature such that the lens adheres to it.

3. The method of claim 1 wherein an inside face of the folded lens is facially engaged with the blade and is cooled to a lower temperature than an outside face of said lens, which is not in contact with the blade,
   the temperature of the outside lens face being cooled less than said inside face, so that said outside face will not freeze to eye tissue.

4. The method of claim 1 wherein cooling is continued after said lens has been frozen, to regulate the thawing of said lens.

5. The method of claim 1 wherein said lens is inserted into an eye while carried on said blade, and
   cooling is applied to said blade while said lens is being so inserted.

6. The method of claim 5 wherein the rate at which cooling is applied to said blade during insertion into the eye is altered to compensate for such insertion.

7. The method of claim 1 wherein said lens is folded in half on said blade.

8. The method of claim 1 wherein said lens is folded around said blade so that no part of the blade projects laterally outward of the lens.

9. A method of implanting a resiliently foldable intraocular lens in an eye, comprising,
   folding the lens around an insertion instrument,
   chilling the folded lens to a temperature substantially below body temperature and sufficiently low to freeze it in the folded configuration, the lens being retained on the insertion instrument by such frozen condition,
   inserting the frozen lens, while carried by the insertion instrument, into the eye through a primary surgical incision, the width of said incision being slightly greater than the width of the lens as frozen on the insertion instrument,
   permitting the lens to thaw within the eye and thereby unfold to its original configuration,
   removing the insertion instrument from the lens,
   centering the lens within the eye after it has been unfolded, and
   withdrawing the insertion instrument from the eye through said primary incision.

10. The method of claim 9 wherein the folded lens is adhered to said insertion instrument.

11. The method of claim 10 wherein said chilling itself adheres the folded lens to the insertion instrument and said thawing releases said lens from said instrument.

12. The method of claim 9 including the further step of controlling the temperature of said insertion implement while said lens is carried thereon, thereby regulating the unfolding of said lens within the eye 13. The method of claim 9 wherein said insertion instrument is in the form of a blade having two opposite faces, one portion of the lens engaging one face of the blade and another portion of the lens engaging a second face of the blade.

14. The method of claim 13 wherein one face of said blade is placed on one portion of the lens and another portion of the lens is folded over the second face of the blade.

15. The method of claim 9 wherein said lens is chilled while on said insertion instrument.

16. The method of claim 9 wherein a second instrument is inserted through a secondary incision in the eye and is engaged with the lens to control said unfolding.

17. The method of claim 16 wherein said second instrument holds said lens away from the cornea of the eye during said unfolding.

18. The method of claim 9 wherein said lens is folded in half o said insertion instrument.

19. A method of implanting a resiliently foldable intraocular lens in an eye, comprising,
    folding the lens to reduce its width,
    chilling the folded lens to a temperature substantially below body temperature and sufficiently low to freeze it in the folded configuration,
    there being no frozen medium around the lens to retain it in the folded configuration, the lens retaining said folded configuration only by reason of being frozen,
    inserting the folded, frozen lens into an eye,
    permitting the lens to thaw within the eye and unfold to its original configuration, and
    centering the unfolded lens within the eye.

20. The method of claim 19 wherein said lens is frozen at a temperature in the range of about $-21°$ to $-60°$ C.

21. A method of implanting a resiliently foldable intraocular lens in an eye, comprising,
    folding the lens to reduce its width,
    chilling the folded lens to a temperature substantially below body temperature and sufficiently low to freeze it in the folded configuration,
    said lens being adhered by said freezing to an instrument for carrying the frozen lens to the eye,
    inserting the folded, frozen lens into an eye,
    permitting the lens to thaw within the eye and unfold to its original configuration, and
    centering the unfolded lens within the eye.

22. The method of claim 21 wherein said instrument is itself chilled, after said lens has been adhered to it, to slow the thawing of said lens.

23. The method of claim 19 wherein the lens is inserted in the eye through a primary incision and wherein said unfolding is assisted with an instrument inserted through a smaller secondary incision.

24. A frozen, folded intraocular lens, said lens formed of a resiliently foldable plastic material which loses flexibility at a temperature substantially below body temperature,
    said lens being folded on itself and being frozen at a temperature substantially below body temperature,
    said lens remaining in such folded configuration while so frozen and being returnable to an unfolded use condition by thawing to a temperature no higher than body temperature,
    there being no frozen medium around the lens to retain it in the folded configuration, the lens retaining said folded configuration only by reason of being frozen.

25. The frozen, folded lens of claim 24 wherein said plastic material is an acrylic composition.

26. The frozen, folded lens of claim 24 wherein said plastic material is a silicone material.

27. The frozen, folded lens of claim 24 wherein said lens is folded in half.

28. A frozen, folded intraocular lens, said lens formed of a resiliently foldable plastic material which loses flexibility at a temperature substantially below body temperature,
    said lens being folded on itself and being frozen at a temperature substantially below body temperature,
    said lens remaining in such folded configuration while so frozen and being returnable to an unfolded use condition by thawing to a temperature no higher than body temperature,
    said lens being folded around an insertion instrument.

29. The frozen, folded lens of claim 28 wherein said lens adheres to said insertion instrument while frozen, said adherency disappearing as said lens approaches body temperature.

30. The frozen, folded lens of claim 28 wherein said insertion instrument has a blade about which said lens is folded.

31. The frozen, folded lens of claim 30 wherein said blade has a cross-sectional configuration approximating a teardrop.

32. The frozen, folded lens of claim 28 further including means connected to said insertion instrument for chilling it and thereby chilling said lens while said lens is folded around said instrument.

33. The frozen, folded lens of claim 32 wherein the means for chilling the insertion instrument is adjustable to regulate the amount of chilling.

* * * * *